(12) United States Patent
Schmalix et al.

(10) Patent No.: US 9,089,532 B2
(45) Date of Patent: Jul. 28, 2015

(54) STABLE DOSAGE FORM OF PHENYLALANINE DERIVATIVES

(75) Inventors: Wolfgang Schmalix, Gröbenzell (DE);
Markus Bürgle, München (DE); Klaus Koch, Mering (DE)

(73) Assignee: Wilex AG, München (DE)

( * ) Notice: Subject to any disclaimer, the term of this patent is extended or adjusted under 35 U.S.C. 154(b) by 817 days.

(21) Appl. No.: 11/631,891

(22) PCT Filed: Sep. 20, 2005

(86) PCT No.: PCT/EP2005/010143
§ 371 (c)(1),
(2), (4) Date: Jan. 8, 2007

(87) PCT Pub. No.: WO2006/032461
PCT Pub. Date: Mar. 30, 2006

(65) Prior Publication Data
US 2007/0244127 A1    Oct. 18, 2007

(30) Foreign Application Priority Data
Sep. 21, 2004 (DE) .......................... 10 2004 045 720

(51) Int. Cl.
| A61K 31/495 | (2006.01) |
| A61K 31/198 | (2006.01) |
| A61K 9/00 | (2006.01) |
| A61K 31/18 | (2006.01) |
| A61K 47/10 | (2006.01) |
| A61K 47/12 | (2006.01) |

(52) U.S. Cl.
CPC ............. *A61K 31/198* (2013.01); *A61K 9/0019* (2013.01); *A61K 31/18* (2013.01); *A61K 31/495* (2013.01); *A61K 47/10* (2013.01); *A61K 47/12* (2013.01)

(58) Field of Classification Search
None
See application file for complete search history.

(56) References Cited

U.S. PATENT DOCUMENTS
2003/0013723 A1 * 1/2003 Wilhelm et al. ......... 514/255.01

FOREIGN PATENT DOCUMENTS
WO    WO 99/05096    2/1999

OTHER PUBLICATIONS

Gennaro; "Remington's Pharmaceutical Sciences"; 1990; 18th Ed., Mack Publishing Co. Easton, PA, pp. 218-219, 241-242, 1549-1550.*
Aboofazeli, et al.; "Transdermal Delivery of Nicardipine: An Approach to In Vitro Permeation Enhancement"; 2002; Drug Delivery; 9: 239-247.*
Jones et al.; "Topical erythromycin vs blank vehicle in a multiclinic acne study"; 1981; Archives of Dermatology; 117(9): 551-3; PubMed abstract; PMID: 6457568.*
Strickley RG. Solubilizing Excipients in Oral and Injectable Formulations. Pharmaceutical Research. 2004; 21(2):201-230).*
Akers MJ. Excipient—Drug Interactions in Parenteral Formulations. Journal of Pharmaceutical Sciences, 2002; 91(11):2283-2300.*
E. L. Jones, et al., "Topical Erythromycin vs Blank Vehicle in a Multiclinic Acne Study," Arch Dermatol, vol. 117, pp. 551-553, Sep. 1981.

* cited by examiner

*Primary Examiner* — Marcos Sznaidman
*Assistant Examiner* — Rayna B Rodriguez
(74) *Attorney, Agent, or Firm* — Greenberg Traurig, LLP

(57) ABSTRACT

The invention relates to improved and stable pharmaceutical formulations of phenylalanine derivatives and the use thereof as urokinase inhibitors, particularly for the treatment of malignant tumors and tumoral metastases.

1 Claim, 7 Drawing Sheets

STABLE DOSAGE FORM OF PHENYLALANINE DERIVATIVES

CROSS REFERENCE TO RELATED APPLICATION

This application is a 35 USC §371 National Phase Entry Application from PCT/EP2005/010143, filed Sep. 20, 2005, and designating the United States.

The invention relates to improved and stable pharmaceutical formulations of phenylalanine derivatives and to the use thereof as urokinase inhibitors, in particular for the treatment of malignant tumours and of tumour metastases.

The ability of solid tumours to propagate and metastasise into surrounding tissue correlates with the degradation or modification of the extracellular matrix (tumour stroma) in the surroundings of the tumour cell or with their ability to penetrate the basal membrane. Although the (pathological) biochemical interrelationships have not yet been definitively clarified, the urokinase plasminogen activator (uPA) and urokinase receptor (uPAR) play a central role. uPA mediates the proteolytic cleavage of plasminogen to plasmin. In turn, plasmin is a protease with a broad spectrum of action which is capable of directly breaking down the components of the extracellular matrix such as fibrin, fibronectin, laminin and the protein skeleton of proteoglycans. Plasmin is moreover capable of activating "latent" metalloproteases and the inactive proenzyme of uPA, pro-uPA.

Tumour cells and non-malignant cells of the tumour stroma synthesise and secrete the enzymatically inactive proenzyme pro-uPA. Proteases, such as for example plasmin or cathepsine B and L, cleave pro-uPA by limited proteolysis to yield the active serine protease HMW-uPA (HMW=high molecular weight). Pro-uPA and the active protease HMW-uPA bind to the cell surface receptor uPAR (CD87). Plasmin(ogen) likewise binds to specific receptors on the plasma membrane of the tumour cell, so focussing and amplifying plasminogen activation in the immediate surroundings of the tumour cell. Invasive cells are thus capable of breaking down the extracellular matrix without removing by proteolysis the support they require for directed movement.

It has been possible to demonstrate in various cellular biological studies that the cell-associated plasminogen activator system is of particular significance within the cascade-like reaction pathways of tumour-associated proteolysis systems (Wilhelm et al., The urokinase/urokinase receptor system: A. new target for cancer therapy? in: Schmitt M., Graeff H., Kindermann G. (eds.): Prospects in Diagnosis and Treatment of Cancer. International Congress Series, Excerpta Medica 1050, Amsterdam, Elsevier (1994) pp. 145-156). It has been observed in cultures of human colon carcinoma cells that their ability to migrate through an extracellular matrix depends on the degree to which the uPA receptors are saturated with active uPA (Hollas et al., Cancer Res. 51 (1991) 3690-3695). Again in a cell culture model, a reduction in the invasive potential of cells has been observed if the proteolytic activity of uPA has been inhibited by PAI-1 (Cajot et al., Proc. Natl. Acad. Sci. USA 87 (1990) 6939-6943) or PAI-2 (Baker et al., Cancer Res. 50 (1990) 4676-4684). A comparable effect has been achieved on inhibition of uPA binding to the cell surface by blocking the receptor by means of proteolytically inactive uPA variants (Cohen et al., Blood 78 (1991) 479-487; Kobayashi et al., Br. J. Cancer 67 (1993) 537-544). Transfecting epidermoidal carcinoma cells with a plasmid which expresses an antisense transcript against part of uPAR also led, by suppression of uPAR synthesis, to a reduction in the invasiveness of these cells (Kook, EMBO J. 13 (1994) 3983-3991). Antibodies directed against uPA and PAI-1 reduced the invasive potential lung cancer cells in vitro (Liu et al., Int. J. Cancer 60 (1995) 501-506).

It has been possible to demonstrate the influence of the plasminogen activator system on the metastasisation process in tumour animal models. For instance, the formation of lung metastases in chicken embryos was almost completely inhibited by the addition of antibodies against uPA (Ossowski and Reich, Cell 35 (1983) 611-619). Metastasising human carcinoma cells were transfected with an expression plasmid which codes for a proteolytically inactive, but uPAR-binding uPA mutant. In a mouse model, it was found that, after injection, the carcinoma cells which synthesised inactive uPA formed a significantly smaller number of metastases in comparison with the non-transfected cells (Crowley et al., Proc. Natl. Acad. Sci. USA 90 (1993) 5021-5025). After administration of uPA antisense oligonucleotides, the intraperitoneal propagation of human ovarian carcinoma cells has furthermore been observed to be inhibited in naked mice (Wilhelm et al., Clin. Exp. Metast. 13 (1995) 296-302).

Recent years have seen intensive investigation of the clinical significance of plasminogen activator system factors (uPA, uPAR, PAI-1 and PAI-2) to the prognosis of patients with solid malignant tumours. In these investigations, uPA antigen content in various tumours (for example breast, ovary, stomach, lungs, kidneys etc.) was found to be a strong predictor both of relapse-free survival and of death (see for example Schmitt et al., J. Obstet. Gynaecol. 21 (1995) 151-165 Jaenicke et al., Breast Cancer Res. Treat. 24 (1993) 195-208; Kuhn et al. Gynecol. Oncol. 55 (1994) 401-409; Nekarda et al., Lancet 343 (1994) 117 Pedersen et al., Cancer Res. 54 (1994) 4671-4675). Elevated concentrations of uPAR in lung (Pedersen et al., above) and breast cancer tissue (Duggan et al., Int. J. Cancer 61 (1995) 597-600; Ronne et al., Breast Cancer Res. Treat. 33 (1995) 199-207) and in stomach cancer both in the tumour tissue itself (Heiss et al., J. Clin. Oncol. 13 (1995) 2084 2093) and in tumour cells shed into the bone marrow (Heis: et al., Nature Medicine 1 (1995) 1035-1039) likewise correlate with a poor prognosis.

It has also been found that 3-amidinophenylalanine derivatives substituted in position 2 with a phenyl residue are selective uPA inhibitors which are active in vivo (EP 1 098 651). In animal experimentation, these compounds are administered in the form of aqueous solutions.

WO 02/074756 and WO 03/103644 disclose the use of further phenylalanine-based urokinase inhibitors as well as the use of 3-guanidinophenylalanine derivatives as urokinase inhibitors.

It has been found in the course of the first clinical trials of the above-stated compounds that administration in the form of aqueous mannitol, for example D-mannitol, without the addition of solutions containing organic solvents and propylene glycol/ethanol and common salt is associated with disadvantages. For instance, it is not possible to produce a stable concentrated active ingredient solution, whether in saline solutions or using the isotonising agent mannitol, which does not have a tendency to precipitate and form deposits. Thus, for example in five (5) percent mannitol solutions, a precipitate consisting of the added active ingredient forms after extended storage. Formulations consisting of purely organic solvents have proved equally unsuitable, as the active ingredient does not exhibit the requisite chemical stability therein and has a tendency to decompose. Accordingly, after approx. 1.5 months, the active ingredient begins to break down by amide formation to yield the ester, so making the active ingredient solution unusable.

WO 2004/011004 discloses an approach to stabilising aqueous solutions containing phenylalanine-based urokinase inhibitor in the form of "liposomes", mixed micelles consisting of various phospholipids. This type of stabilisation is, however, not adequate for all applications, the chemical stability of the liposomal formulation no longer being adequately ensured in particular after reconstitution with physiological buffers.

Preliminary testing for the development of a new formulation revealed very good solubility of the active ingredient Nα-(2,4,6-triisopropylphenylsulfonyl)-3-amidino-(L)-phenylalanine-4-ethoxycarbonylpiperazide (WX-UK1) in polyols, for example diols, and in mixtures of polyol/alcohol and water (Table 1).

These data revealed that mixtures of polyol and alcohol, such as for example propylene glycol (PG) and ethanol (EtOH), are good solvents for a liquid formulation. Both solvents are additionally suitable for parenteral administration of active ingredients.

The storage of different formulations, for example
a) WX-UK1 60 mg/ml in PG/EtOH/water 40/10/50
b) WX-UK1 50 mg/ml in PG/EtOH/water 40/10/50
c) WX-UK1 40 mg/ml in PG/EtOH/water 40/10/50
d) WX-UK1 20 mg/ml in PG/EtOH/water Oct. 10, 1980
e) WX-UK1 4 mg/ml in water (control)
f) WX-UK1 4 mg/ml in 5% D-mannitol (control)
at two to eight degrees Celsius (2-8° C.) showed that an acicular crystalline precipitate forms after just a few hours in formulation (e) and (f). After four (4) days at two to eight degrees Celsius (2-8° C.) a precipitate of similar appearance also forms in formulation (d).

In formulations (a) and (b), no precipitate is found after 16 or 22 days' storage at two to eight degrees Celsius (2-8° C.).

In stability studies at 2-8° C., 25° C./60% RH (relative humidity) and 40° C./75% RH, under the 40° C. conditions, formulation (c) exhibits an impurity content of approx. 4% after just 6 weeks, of approx. 23% after 8 weeks and of approx. 38% after 12 weeks, in comparison with a content of approx. 0.5% at the beginning of the investigation. At the same time, the pH value of the formulation rose from 5.1 to 8.7 over a period of 12 weeks (FIG. 1).

The rise in the pH value is probably attributable to the breakdown of WX-UK1 FIG. 2 shows a possible breakdown reaction of the active ingredient WX-UK1 in aqueous media: WX-UK1 breaks down in the first step to the corresponding WX-UK1 amide, ammonia being liberated but scavenged in the form of ammonium chloride because WX-UK1 is present as the hydrochloride. In the second breakdown step, the WX-UK1 amide reacts with alcohol to liberate further ammonia to form the corresponding WX-UK1 ester. The liberation of ammonia is probably responsible for the rise in pH value.

On the basis of the findings regarding the breakdown process, preferably anhydrous formulations were taken into consideration in order to avoid the decomposition of the active ingredient brought about by water. The relatively high viscosity of the purely organic solvents does, however, complicate handling of the high viscosity concentrates in day to day clinical practice. Moreover, the strongly hygroscopic properties of polyols lead to the uptake of water, so restarting the active ingredient breakdown process. Buffering with organic buffers, such as for example triethanolamine/HCl, piperazine/HCl, propionic acid/propionate, not all of which are physiologically acceptable, is also problematic.

Attempts to stabilise aqueous solutions by the addition of surface-active agents, such as for instance Pluronic F68 or Tween 80, or stabilisers, such as human serum albumin, were fruitless. Adding cosolvents, such as polyethylene glycols, and formulating the active ingredient in mixed micelles containing bile salt glycocholate monohydrate and the phospholipid egg phosphatidyl choline, also failed to provide adequate stability.

There was accordingly a requirement to provide novel pharmaceutical formulations for active ingredients comprising amidino and/or guanidino groups, which formulations are, on the one hand, both physically and chemically stable and exhibit good handling and storage properties in portions and/or as a concentrate, in order to prepare, when required, stable pharmaceutical preparations, for example stable physiological infusion solutions with suitable isotonising agents, which preparations are acceptable and exhibit elevated activity.

Said object is achieved according to the invention by a pharmaceutical formulation according to claim 1, comprising (i) an amidino-, hydroxyamidino-, guanidino- and/or hydroxyguanidinophenylalanine derivative as active ingredient, (ii) an alcohol or a polyol or a mixture thereof and (iii) an aqueous phase comprising a buffer.

The active ingredient used is preferably a phenylalanine derivative having a serine protease inhibitory action, in particular urokinase inhibitory action.

Preferred active ingredients are the amidinophenylalanine or guanidinophenylalanine compounds disclosed in EP-A-1 098 651, WO 02/074756 and WO 03/103644. Hydroxyamidinophenylalanine or hydroxyguanidinophenylalanine compounds, as disclosed in PCT/EP2004/005682, are likewise preferred. Suitable active ingredients of the pharmaceutical formulation according to the invention are in particular the novel urokinase inhibitors, derived from 3-amidinophenylalanine or 3-guanidinophenylalanine, of the general formula I,

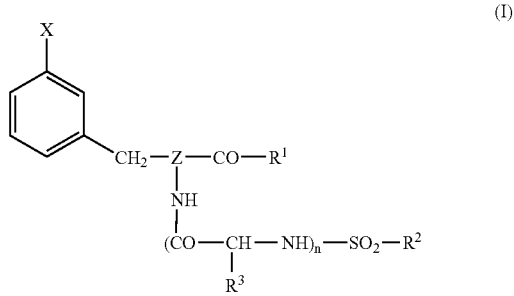

(I)

which assume the form not only of racemates but also of L or D configured compounds and in which X is an amidino or guanidino group or hydroxyamidino or hydroxyguanidino group, R$^1$
(a) is OH or OR$^4$, wherein R$^4$ is a branched or unbranched C$_1$-C$_8$ alkyl, C$_3$-C$_8$ cycloalkyl or aralkyl, for example benzyl or phenylethyl, which is optionally substituted, for example, with hydroxyl, carboxyl, sulfonyl, nitro, cyano, oxo and/or halogen,
(b) represents a group of the formula

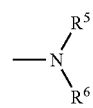

in which R$^5$ and R$^6$ are any desired residues compatible with the overall structure, wherein in particular
(i) R$^5$ and R$^6$ are H,
(ii) R$^5$ is H and R$^6$ is a branched or unbranched C$_1$-C$_8$ alkyl, aralkyl, for example benzyl or phenylethyl, or $C_5$-$C_8$ cycloalkyl, which is optionally substituted, for example, with hydroxyl, carboxyl, sulfonyl, nitro, cyano, oxo and/or halogen,
- (iii) $R^5$ and $R^6$ are in each case independently an unbranched or branched $C_1$-$C_4$ alkyl optionally substituted, for example, with hydroxyl and/or halogen or
- (iv) $R^5$ is H and $R^8$ is —$NH_2$ or an amino group in particular substituted with aryl or heteroaryl,
- (v) $R^5$ is H or an unbranched or branched $C_1$-$C_4$ alkyl which is optionally substituted, for example, with hydroxyl and/or halogen, and $R^6$ is the residue of an amino acid, for example an α-, β- or ω-aminocarboxylic or aminosulfonic acid, or the residue of a peptide, for example with a length up to 50 amino acids or of a polypeptide, for example with a length of more than 50 amino acids to 1,000 amino acids, (c) represents a group of the formula

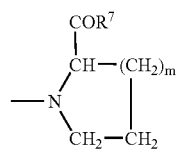

in which m denotes the number 1 or 2, and in which one or more of the methylene groups are optionally substituted, for example with a hydroxyl, carboxyl, $C_1$-$C_4$ alkyl or aralkyl residue, for example benzyl or phenylethyl, wherein the group (c) is racemic or D or L configured, and $R^7$ has the meaning of $R^1$ in indents (a), (b) and (f), (d) represents a group of the formula

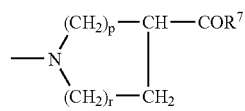

in which p=r=1, p=1 and r=2 or p=2 and r=1 and in which one or more of the methylene groups are optionally substituted, for example, with a hydroxyl, carboxyl, $C_1$-$C_4$ alkyl or aralkyl residue, for example benzyl or phenylethyl, and $R^7$ has the meaning of $R^1$ in indents (a), (b) and (f), (e) represents a piperidyl group, which is optionally substituted in one of positions 2, 3 and 4, for example, with a $C_1$-$C_4$ alkyl, $C_1$-$C_3$ alkoxy or hydroxyl residue, wherein a further aromatic or cycloaliphatic ring, preferably phenyl or cyclohexyl, is optionally fused in 2,3 or 3,4 position, relative to the heteroatom, onto the heterocycloaliphatic rings of the formulae (c), (d), (e), (f) represents a group of the formula

in which $R^8$
- (i) means a $C_1$-$C_6$ alkyl residue, such as for example ethoxycarbonyl, or aryl residue, such as for example phenyl, p-halophenyl, naphthyl, which is optionally substituted, for example, with $C_1$-$C_6$ alkyl, $C_1$-$C_3$ alkoxy, hydroxyl, carboxyl, sulfonyl, nitro, cyano, oxo and/or halogen,
- (ii) means a saturated or unsaturated, branched or unbranched $C_1$-$C_6$ alkoxy residue or
- (iii) means a phenoxy- or benzyloxycarbonyl residue which is optionally substituted, for example, with $C_1$-$C_6$ alkyl, $C_1$-$C_3$ alkoxy, hydroxyl, carboxyl, sulfonyl, nitro, cyano, oxo and/or halogen, (g) represents an acyl residue of the formula —COX, wherein X
- (i) means H, an unbranched or branched alkyl residue, preferably a $C_1$-$C_6$ alkyl residue, in particular methyl, which is optionally substituted, for example, with hydroxyl, carboxyl, sulfonyl, nitro, cyano, oxo and/or halogen,
- (ii) means an aryl or heteroaryl residue, such as for example phenyl, p-halophenyl, thienyl, which is optionally substituted, for example, with $C_1$-$C_6$ alkyl, $C_1$-$C_3$ alkoxy, hydroxyl, carboxyl, sulfonyl, nitro, cyano, oxo and/or halogen or
- (iii) means a cycloalkyl residue, preferably a $C_3$-$C_{10}$ cycloalkyl residue, which is optionally substituted, for example, with hydroxyl, carboxyl, sulfonyl, nitro, cyano, oxo and/or halogen, (h) represents an aralkyl residue, for example benzyl or phenylethyl, in which the aromatic residue is optionally substituted, for example, with a halogen atom, a $C_1$-$C_6$ alkyl, $C_1$-$C_3$ alkoxy, hydroxy, cyano, carboxyl, sulfonyl or nitro group, (i) represents a carboxamide residue of the formula —CONR'R", a thiocarboxamide residue —CSNR'R" or an acetamide residue —$CH_2$—CONR'R", wherein
- (i) R' and R" are H,
- (ii) R' and R" are in each case independently $C_1$-$C_4$ alkyl,
- (iii) R' is H and R" is $C_1$-$C_4$ alkyl,
- (iv) R" is H and R" is aryl, for example phenyl, or
- (v) R' and R" form, with the nitrogen atom, a heterocycloaliphatic ring with 5-7 ring members, which may bear a further heteroatom, for example N, O and/or S, (j) represents an $SO_2$—Y residue, in which Y
- (i) is a $C_1$-$C_8$ alkyl which is optionally substituted, for example, with hydroxyl, carboxyl, sulfonyl, nitro, cyano, oxo and/or halogen, preferably methyl, trifluoromethyl, trichloromethyl,
- (ii) is an aryl or heteroaryl which is optionally substituted, for example, with $C_1$-$C_6$ alkyl, $C_1$-$C_3$ alkoxy, hydroxyl, carboxyl, sulfonyl, nitro, cyano, oxo and/or halogen, such as for example phenyl, 4-methylphenyl, 2,4,6-trimethylphenyl, 2,4,6-triisopropylphenyl, 4-methoxy-2,3,6-trimethylphenyl, 2,2-dimethyl-6-methoxy-chromanyl, 2,2,5,7,8-pentamethylchromanyl, anthraquinonyl, naphthyl or quinolyl, or O-aryl, preferably O-phenyl, or O-heteroaryl or
- (iii) is —NRR", wherein R' and R" in each case independently mean H or $C_1$-$C_3$ alkyl, (k) represents a cycloaliphatic ring with 5 to 8 C atoms, which is optionally substituted, for example, with a $C_1$-$C_6$ alkyl, $C_1$-$C_3$ alkoxy, halogen, hydroxyl and/or oxo group, (l) represents a heteroaryl residue, which is optionally substituted, for example, with $C_1$-$C_6$ alkyl, $C_1$-$C_3$ alkoxy, hydroxyl, carboxyl, sulfonyl, nitro, cyano, oxo and/or halogen, such as for example pyridyl or pyrimidyl, or heterocycloaliphatic residue, for example N-methylpiperidyl, (m) represents a functionalised alkyl residue of the formula —(CH$_2$)$_n$—X, wherein the alkyl chain is unbranched or branched, n means 1 to 8 and the functional residue X
(i) represents a hydroxyl group, the H atom of which is optionally substituted by a C$_1$-C$_4$ alkyl, aralkyl, for example benzyl or phenylethyl, aryl, for example phenyl, C$_1$-C$_4$ hydroxyalkyl or acyl group, CO-alkyl (C$_1$-C$_6$),
(ii) means a halogen atom,
(iii) represents a tertiary amino group of the formula —N(alk)$_2$, wherein the alkyl groups have 1 to 3 C atoms and preferably have the same meaning and the nitrogen atom belongs to a heterocycloaliphatic ring with 5-7 ring members, which may bear a further heteroatom, for example N, O and/or S, R$^2$ represents a phenyl residue which is optionally substituted, for example, with C$_1$-C$_6$ alkyl, C$_1$-C$_3$ alkoxy, hydroxyl, carboxyl, sulfonyl, nitro, cyano, oxo and/or halogen, such as for example phenyl, 4-methylphenyl, 2,4,6-trimethylphenyl, 2,4,6-triisopropylphenyl, 4-methoxy-2,3,6-trimethylphenyl, R$^3$ is H or branched or unbranched C$_1$-C$_4$ alkyl and n means 0 or 1, Z means N or CR$^9$, wherein R$^9$ is H or branched or unbranched C$_1$-C$_4$ alkyl.

The compounds may also be present as salts, preferably as physiologically acceptable acid salts, for example as salts of mineral acids, particularly preferably as hydrochlorides, hydrogensulfates, sulfates or as salts of suitable organic acids.

Of the compounds defined in the general claims, those which are of particular significance are those in which R$^1$ corresponds to a group of the formulae (b), (d) and (f), R$^2$ represents a phenyl residue mono-, di- or trisubstituted by alkyl, in particular a 2,4,6-substituted phenyl residue, for example a 2,4,6 triisopropylphenyl residue, and n=0. Further preferred compounds are those in which Z is CH or N.

The compound of the formula (I) particularly preferably comprises Nα-(2,4,6-triisopropylphenylsulfonyl)-3-amidino-(D,L)-phenylalanine-4-ethoxycarbonylpiperazide, Nα-(2,4,6-triisopropylphenylsulfonyl)-3-guanidino-(D,L)-phenylalanine-4-ethoxycarbonylpiperazide or the L-entantiomers thereof or a pharmaceutically acceptable salt of these compounds.

As mentioned above, corresponding hydroxy compounds of the amidino- and guanidinophenylalanine derivatives are also suitable as active ingredients, for example those as are disclosed in PCT/EP2004/005682, in particular compounds of the general formula II and/or III

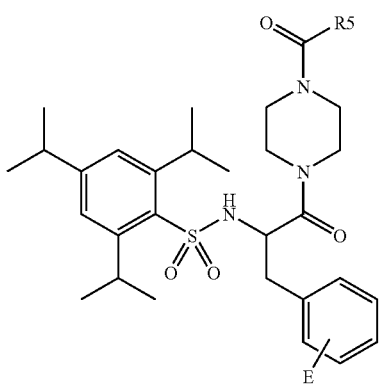

(II)

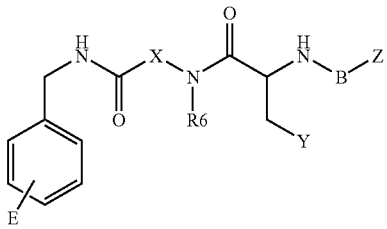

(III)

in which

E means a group from

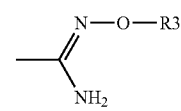

(Am)

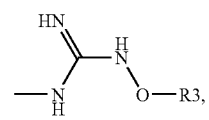

(Gua)

B means —SO$_2$— or —CO—,

X means —NR$^1$ or —CHR$^1$,

Z means —R$^4$, —OR$^4$ or —NH—R$^4$,

Y means —OR$^2$ or —NHR$^2$,

R$^1$ in each case independently means —H, —C$_1$-C$_6$ alkyl, —C$_2$-C$_6$ alkenyl or —C$_2$-C$_6$ alkynyl, unsubstituted or substituted, R$^2$ means —H, —OR$^1$, —COR$^1$, —COOR$^1$ or —CON(R$^1$)$_2$, R$^3$ means —H, —C$_1$-C$_6$ alkyl, —C$_2$-C$_6$ alkenyl or —C$_2$-C$_6$ alkynyl, unsubstituted or substituted, or —COR$^6$ or —COOR$^6$ or an oligo- or polyalkyleneoxy residue comprising for example 2-50 C$_2$-C$_4$ alkyleneoxy, for example ethyleneoxy, residues, R$^4$ means —H, —C$_1$-C$_6$ alkyl, —C$_2$-C$_6$ alkenyl or —C$_2$-C$_6$ alkynyl, unsubstituted or substituted, or a cyclic residue and R$^5$ means —OR$^6$, —N(R$^6$)$_2$, —C$_1$-C$_6$ alkyl, —C$_2$-C$_6$ alkenyl or —C$_2$-C$_6$ alkynyl, unsubstituted or substituted, and R$^6$ means —H, —C$_1$-C$_6$ alkyl, —C$_2$-C$_6$ alkenyl or —C$_2$-C$_6$ alkynyl, unsubstituted or substituted, or a cyclic residue, wherein each cyclic residue may bear one or more substituents, for example selected from among —C$_1$-C$_3$ alkyl, —OR$^6$ (for example —OH or —C$_1$-C$_3$ alkoxy), halogen, =O, —NO$_2$, —CN, —COOR$^6$, —N(R$^6$)$_2$, —NR$^6$COR$^6$, —NR$^6$CON(R$^6$)$_2$ and —OCOR$^6$, and wherein each alkyl, alkenyl and alkynyl may be linear or branched and may bear one or more substituents, for example selected from among halogen (F, Cl, Br, I), —OR$^6$, —OCOR$^6$, —N(R$^6$)$_2$, —NR$^6$COR$^6$, COOR$^6$, —NR$^6$COR$^6$ or a cyclic residue, or salts of these compounds and optionally pharmaceutically conventional carriers, diluents and/or auxiliaries.

Preferred compounds are those of the general formula IV

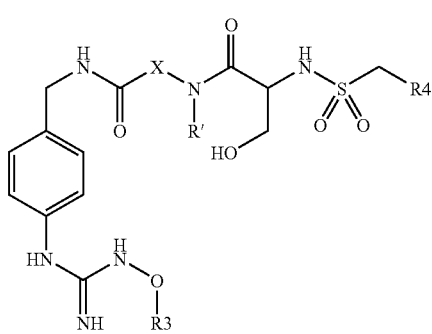

IV in which
X, $R^1$, $R^3$, $R^4$ and $R^6$ are defined as above,
or the salts thereof.

Group E is preferably located in para position of the phenyl ring in compounds I and II. Particularly preferred compounds are those of the general formula I in which E is Am.

The compounds according to the invention comprise a modified amidino or guanidino function E, preferably a hydroxyguanidino or hydroxyamidino function. Such modifications have only been known as synthesis intermediates in the production of urokinase inhibitors of the guanidino or amidino type. Pharmaceutical activity has not hitherto been suspected.

The compounds may be present as salts, preferably as physiologically acceptable acid salts, for example salts of mineral acids, particularly preferably as hydrochlorides or hydrogensulfates, or as salts of suitable organic acids, for example of organic carboxylic or sulfonic acids, such as for instance tartrates, mesylates or besylates. Hydrogensulfates are particularly preferred. The compounds may be present as optically pure compounds or as mixtures of enantiomers and/or diastereomers.

Cyclic residues may contain one or more saturated, unsaturated or aromatic rings. Preferred examples of cyclic residues are cycloalkyl residues, aryl residues, heteroaryl residues and bicyclic residues. Mono- or bicyclic residues are particularly preferred. The cyclic residues contain preferably 4 to 30, in particular 5-10 carbon atoms and heteroatoms as ring atoms, and optionally one or more substituents as previously stated. Heterocyclic systems preferably contain one or more O, S and/or N atoms. Preferred bicyclic ring systems are those with a —CO— residue.

Alkyl, alkenyl and alkynyl groups preferably contain up to 4 carbon atoms. $R^1$ is preferably H or an optionally substituted $C_1$-$C_4$ alkyl residue, for example —$CH_3$ or a $C_1$-$C_6$ alkylaryl residue, such that —CO—X—$NR^1$ may, for example, represent a glycyl, alanyl, phenylalanyl or homophenylalanyl residue. $R^2$ is particularly preferably H or a $C_1$-$C_3$ alkyl residue, such that Y may, for example, represent an OH or O—$C_1$-$C_3$-alkyl residue. $R^3$ is particularly preferably H. In the compounds I, $R^5$ preferably means —$NHR^5$, particularly preferably —$NH(C_1$-$C_5)$-alkyl, unsubstituted or substituted, for example —$NHC_2H_5$ or —$OR^6$, particularly preferably —$O(C_1$-$C_3)$-alkyl, unsubstituted or substituted, for example ethyloxy or benzyloxy, or —O-aryl, for example phenyloxy. In compounds II and III, $R^6$ is preferably —H or $C_1$-$C_3$ alkyl.

Preferred compounds are those in which the structural element Z denotes $R^4$, in which $R^4$ means an alkyl residue with a cyclic substituent, for example an optionally substituted phenyl residue or a bicyclic residue, such as for instance

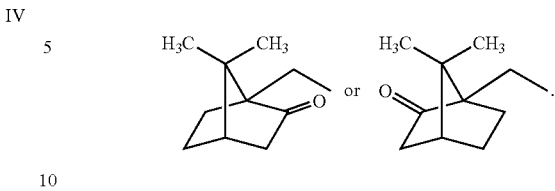

Particularly preferred compounds are those in which $R^4$ means a substituted or unsubstituted $C_1$-$C_3$ alkylaryl residue means, for example a benzyl residue, which may optionally be substituted in meta or para position with halogen and/or —$NO_2$, wherein the halogen is selected from among F, Cl, Br and I, particularly preferably Cl and Br.

The most highly preferred compounds are:
N-α-(2,4,6-triisopropylphenyl-sulfonyl)-3-hydroxyamidino-(L)-phenylalanine-4-ethoxycarbonylpiperazide (WX-671),
N-α-(2,4,6-triisopropyl-phenylsulfonyl)-3-hydroxyamidino-(D)-phenylalanine-4-ethoxycarbonylpiperazide,
N-α-(2,4,6-triisopropylphenylsulfonyl)-3-hydroxyamidino-(D,L)-phenylalanine-4-ethoxycarbonylpiperazide,
N-α-(2,4,6-triisopropylphenylsulfonyl)-3-hydroxyguanidino-(L)-phenylalanine-4-ethoxycarbonylpiperazide (WX-683),
N-α-(2,4,6-triisopropylphenylsulfonyl)-3-hydroxyguanidino-(D)-phenylalanine-4-ethoxycarbonylpiperazide,
N-α-(2,4,6-triisopropylphenyl-sulfonyl)-3-hydroxyguanidino-(D,L)-phenylalanine-4-ethoxycarbonylpiperazide,
N-α-(2,4,6-triisopropylphenylsulfonyl)-3-hydroxy-guanidino-(L)-phenylalanine-4-ethylaminocarbonylpiperazide (WX-685),
N-α-(2,4,6-triisopropylphenylsulfonyl)-3-hydroxyguanidino-(D)-phenylalanine-4-ethylaminocarbonylpiperazide,
N-α-(2,4,6-triisopropylphenylsulfonyl)-3-hydroxyguanidino-(D,L)-phenylalanine-4-ethylaminocarbonylpiperazide, benzylsulfonyl-(D)-Ser-Gly-(4-hydroxyguanidinobenzyl)amide (WX-678), 4-chlorobenzylsulfonyl-(D)-Ser-N-Me-Ala-(4-hydroxyguanidinobenzyl)amide,
4-chlorobenzylsulfonyl-(D)-Ser-Gly-(4-hydroxyguanidinobenzyl)amide benzylsulfonyl-(D)-Ser-N-Me-Gly-(4-hydroxyguanidinobenzyl)amide,
4-chlorobenzylsulfonyl-(D)-Ser-Ala-(4-hydroxyguanidinobenzyl)amide and the salts thereof, for example the hydrogensulfates, such as for instance WX-671.$HSO_4$.

The formulations according to the invention contain a therapeutically active quantity of the active ingredient based on a phenylalanine derivative, a physiologically acceptable quantity of the alcohol and/or polyol, an aqueous phase with buffer constituents and optionally isotonising agents and further auxiliary substances individually or in mixtures or combinations thereof.

The formulations according to the invention preferably contain the active ingredient in a proportion by weight of 0.5 to 10%, preferably of 1 to 9%, particularly preferably of 2 to 5%, relative to the total weight of the formulation.

The active ingredient is preferably present in a concentration of up to 100 mg/ml, preferably up to 80 mg/ml, preferably up to 60 mg/ml, preferably up to 50 mg/ml, more preferably up to 40 mg/ml, still more preferably approx. 30 mg/ml, still more preferably approx. 20 mg/ml, still more preferably approx. 10 mg/ml, still more preferably approx. 4 mg/ml, still more preferably to approx. 1 mg/ml, preferably up to approx. 0.1 mg/ml. The formulation may optionally be further diluted before use.

The alcohol or the polyol for the purposes of the present invention comprise physiologically acceptable mono- and polyhydric alcohols. A polyol is here taken to mean a polyhydric alcohol. In particular, it may be a dihydric alcohol (diol) or a trihydric alcohol (triol), or also a polyhydric alcohol.

Ethanol is, for example, preferred as a monohydric alcohol. Other physiologically acceptable alcohols may, however, also be used.

Polyols which may in particular be considered are physiologically acceptable diols and triols, an example of a preferred triol being glycerol. Glycols are also suitable according to the invention. Examples of glycols are glycol, propylene glycol, polyethylene glycol.

The alcohol and/or the polyol are preferably present in the pharmaceutical formulation according to the invention in such a quantity that this component constitutes approx. 20-60%, preferably 40-60%, more preferably 45-55%, most preferably approx. 50% relative to the volume of the entire formulation.

A mixture of polyol and alcohol is particularly preferred. The ratio of polyol:alcohol is here preferably from 2:1 to 10:1, more preferably 3:1 to 8:1, still more preferably 4:1 to 6:1 and most preferably 4:1.

The mixture preferably comprises a mixture of a glycol and ethanol. A mixture of propylene glycol and ethanol and of polyethylene glycol and ethanol is particularly preferred.

The aqueous phase, comprising a buffer, is preferably selected from a group of physiologically acceptable buffers, in particular acetate buffer, citrate buffer, phosphate buffer and the like; the buffer component preferably comprising a sodium acetate buffer. Other acetate buffers are, however, also suitable, for example potassium acetate buffer, calcium acetate buffer. The person skilled in the art is capable of selecting a suitable buffer from among physiologically acceptable buffers, in particular acetate buffers.

The aqueous phase is preferably present in a quantity of up to 70% relative to the volume of the entire formulation, preferably of up to 60%, more preferably of up to approx. 50%. Of course, the pharmaceutical formulation may, if necessary, be diluted before use. The formulation is preferably diluted immediately before use, preferably with an isotonising agent or an isotonic liquid, such that an isotonic solution suitable for infusion or injection is preferably produced.

The buffer is preferably present in a concentration of up to 1000 mM, preferably up to 500 mM, more preferably up to 250 mM, more preferably up to 200 mM, still more preferably of approx. 100 mM.

The formulation according to the invention may additionally comprise an isotonising agent and/or further auxiliary substances, which are familiar to the person skilled in the art.

The isotonising agent is preferably a sugar or preferably selected from among, for example, glucose, ribose, sucrose, sorbitol, mannitol, lactose, dextrose, trehalose, glycerol and mixtures thereof. The isotonising agent is preferably present in the form of a solution. The isotonising agent used is preferably an approx. 1 to 10%, preferably 2 to 7%, particularly preferably 5% solution. A glucose solution is particularly preferred.

The formulation according to the invention may furthermore contain auxiliary substances which the person skilled in the art may readily determine.

It is furthermore preferred for the formulation according to the invention, at least the aqueous component thereof, to have a pH value in the range from 3.5 to 9.0, preferably a pH value in the range from 4 to 7, and particularly preferably a pH value in the range 4.5 to 5.5.

The formulation according to the invention may be used for various routes of administration, for example as a liquid formulation, parenterally, as an infusion, intramuscularly, intravenously, subcutaneously etc. The formulation is preferably administered intravenously or intramuscularly. The auxiliary substances suitable for this purpose may readily be determined by the person skilled in the art.

The formulation according to the invention may optionally be used in combination with other active ingredients, for example cytostatic or cytotoxic agents, for example doxorubicin, cisplatin, 5-fluoro-uracil or antibodies and peptides.

The formulation according to the invention may be used for parenteral administration, for example for intravenous or intramuscular injection and/or for infusion. The daily dose is preferably 5-250 mg, particularly preferably 20-120 mg in the case of subcutaneous or intramuscular administration and 10-500 mg, particularly preferably 50-250 mg in the case of intravenous administration, in each case relative to an average body weight of 70 kg. Administration proceeds preferably once daily to once weekly.

The present invention also provides a concentrate consisting of a formulation according to the invention, wherein the active ingredient is present in a concentration of up to 100 mg/ml, preferably of up to 80 mg/ml, more preferably of up to 50 mg/ml, still more preferably of approx. 40 mg/ml. The buffer is preferably present in a concentration of up to 1000 mM, preferably of up to 500 mM, more preferably of up to 250 mM, still more preferably of approx. 100 mM.

A concentrate in which the concentration of the active ingredient is 40 mg/ml and the concentration of the buffer 100 mM is particularly preferred.

The concentrates and formulations according to the invention may be stored without major loss of purity and active ingredient for an extended period, typically at two to eight (2-8)° C. but also on storage at elevated temperature, for example at 40° C.

The active ingredient compounds are suitable for combating diseases which are associated with pathological overexpression of uPA and/or urokinase plasminogen activator receptor (uPAR). They are, for example, capable of highly effectively inhibiting the growth and/or propagation of malignant tumours and the metastasisation of tumours. The uPA inhibitors may here optionally be used together with other antitumour agents or with other types of treatment, for example irradiation or surgery. The inhibitors are furthermore also active in other uPA-associated and/or uPAR-associated diseases.

These compounds are capable of highly effectively inhibiting the growth and/or propagation of malignant tumours, for example tumour propagation in pancreatic carcinoma, tumour growth in mammary carcinoma and the metastasisation of tumours.

The inhibitors according to the invention are furthermore also active in other uPA-associated diseases, for example for combatting diseases such as arthritis, inflammation, osteoporosis, retinopathies, for example age-related macular degeneration, in preventing blistering in the skin condition pemphigus vulgaris.

Administration preferably proceeds jointly, for example as a pre- and/or post-treatment, and concurrently in association with surgery, radiation treatment and/or chemotherapy.

The present invention also provides the use of a concentrate according to the invention for the production of an active ingredient solution suitable for injection or infusion by dilution in suitable isotonising agents, wherein a 5% glucose solution is preferably used and the active ingredient concentration preferably amounts to up to 1 mg/ml.

The formulation according to the invention is used for combatting urokinase-associated diseases, in particular for combatting tumours, for example for combatting mammary carcinoma and pancreatic carcinoma and/or metastasisation.

The present invention also provides a method for stabilising pharmaceutical formulations comprising a compound which comprises an amidino, hydroxyamidino, guanidino and/or hydroxyguanidino group, preferably amidino- and/or guanidinophenylalanine derivatives or the hydroxy compounds thereof, by addition of a suitable quantity of a polyol or an alcohol or a mixture thereof, and an aqueous phase comprising a buffer. An isotonising agent is preferably additionally added.

The alcohol, the polyol, the buffer and the isotonising agent are as described above.

The active ingredient used is preferably an amidino- and/or guanidinophenylalanine derivative having a urokinase inhibitory action, as described above.

The following Examples are intended to illustrate the invention but without limiting it in any manner.

EXAMPLES

Example 1 pH-Dependency of Active Ingredient Breakdown

Figure 3:
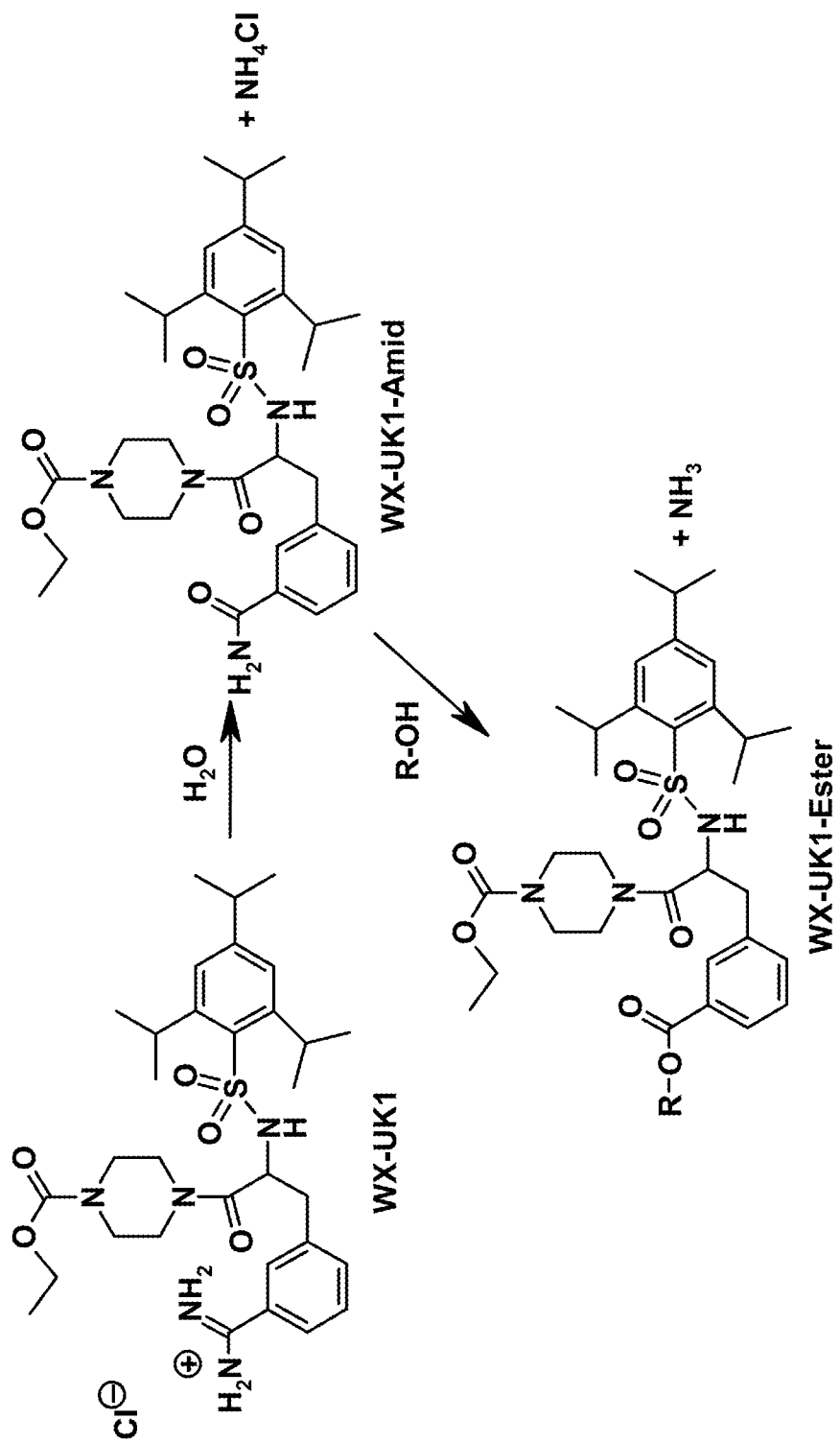
FIG. 3 shows the potential breakdown mechanism for WX-UK1 in aqueous solution.

The pH-dependency of active ingredient breakdown (WX-UK1) was investigated at three different pH values with heat treatment at 60° C. by dissolving 2.5 mg of WX-UK1 in 1 ml of ethanol/water (1:1 vol/vol). This solution was aliquoted into three vessels. One aliquot was adjusted to pH 2 by addition of 20 µl of 1 N hydrochloric acid, a second aliquot was adjusted to pH 11 by addition of 20 µl of 2 N sodium hydroxide solution and the third aliquot was left at a neutral pH. After incubation, the solutions were analysed at defined points in time (0, 5, 12 and 48 h) by means of a stability-indicating HPLC method. It was found that WX-UK1 remained stable at an acidic pH for the investigated period. At a neutral or basic pH, however, moderate to rapid breakdown of WX-UK1 was observed (FIG. 3).

Example 2

Figure 1:
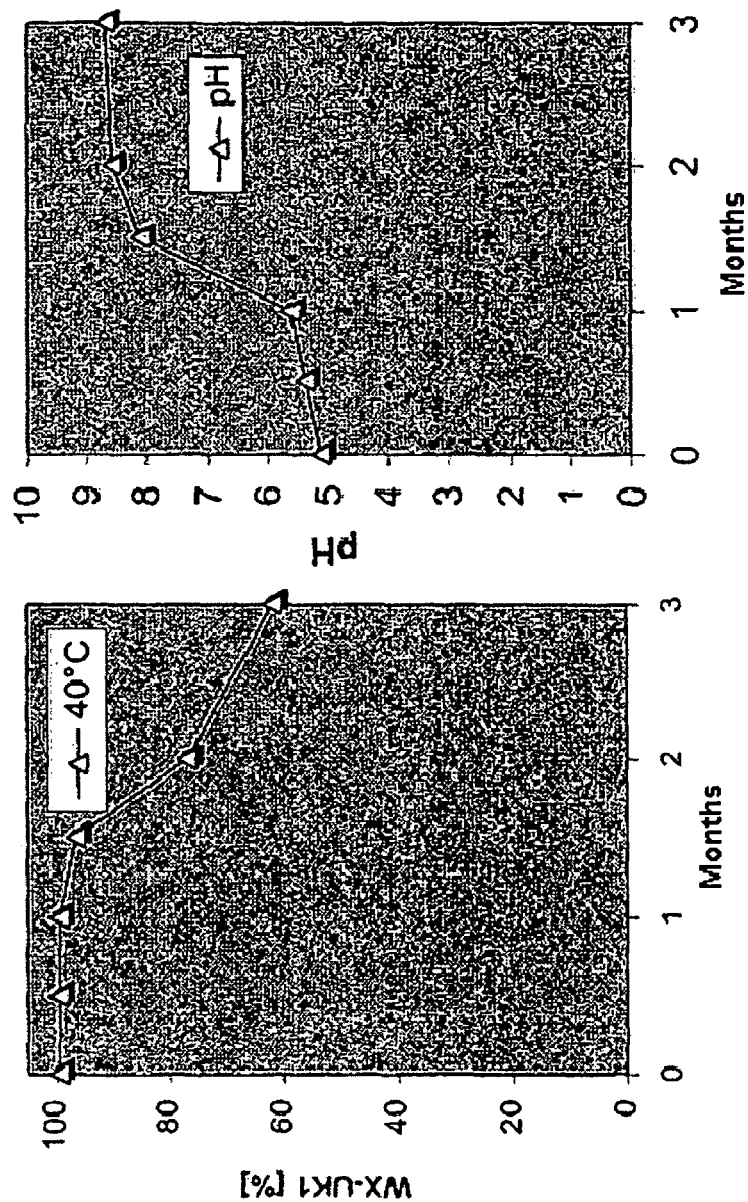
FIG. 1 is a Table showing the maximum solubility of WX-UK1 in various solvents and solvent mixtures.
Figures 2A, 2B:
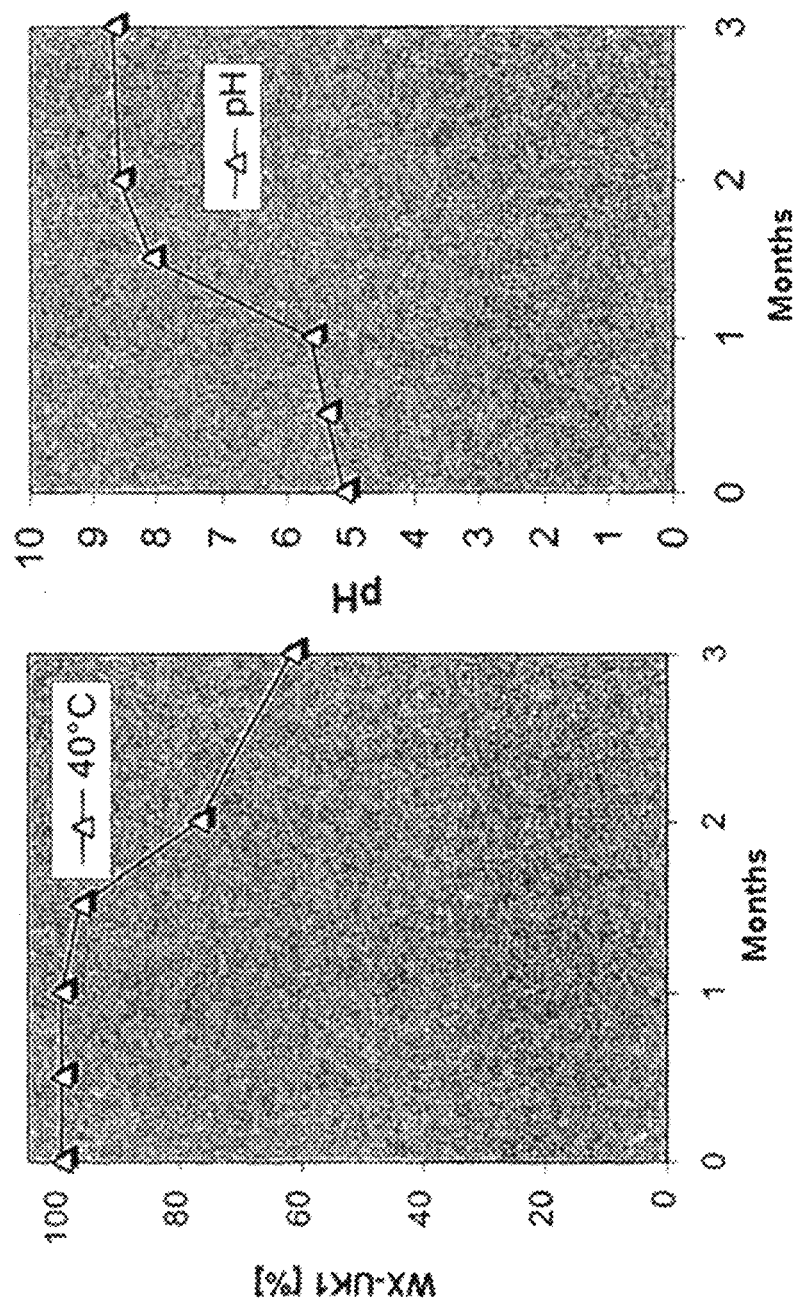
FIGS. 2A and 2B show the variation in WX-UK1 purity (FIG. 2A) and in pH value (FIG. 2B) at 40° C. in PG/EtOH/water (4/1/5).

Active Ingredient Stability in Polyol/Ethanol Formulation 0.4 ml of propylene glycol (PG) and 0.1 ml of ethanol were added in succession to 40 mg of WX-UK1. This solution was made up with 0.3 ml of water and stirred until the WX-UK1 passed into solution and the solution exhibited slight opalescence. The remaining water (approx. 0.2 ml) was then added. The solution was then stored at 40° C. and the pH value and purity of the solution were in each case analysed after a period of 2, 4, 6, 8 and 12 weeks. To this end, 250 µl of the WX-UK1 solution were transferred into a 100 ml measuring flask and made up with water/acetonitrile (50:50 vol/vol) to the graduation mark (concentration: approx. 0.1 mg/ml of WX-UK1). 20 µl of this dilution were then analysed by means of a stability-indicating HPLC method analysed (see Annex). pH value-analysis of the WX-UK1 solution was carried out by means of a potentiometric method at 20-25° C. It was found (FIG. 1) that the higher is the pH value of the solution, the faster WX-UK1 breaks down.

Example 3

Alternative Buffered WX-UK1 Formulations

In each case 5 ml of the following solutions (a) to (e) were produced. The solutions were then stored at 60° C. and the pH value and purity of the solution were in each case analysed after a period of 0, 12, 24, 48 hours. To this end, 250 µl of the WX-UK1 solution were transferred into a 100 ml measuring flask and made up with water/acetonitrile (50:50 vol/vol) to the graduation mark (concentration is approx. 0.1 mg/ml of WX-UK1). 20 µl of this dilution of the WX-UK1 solution were then analysed by means of a stability-indicating HPLC method (see Annex).
a) 1 mg/ml WX-UK1 in water (measure pH value)
b) 40 mg/ml WX-UK1 in PG/ethanol/water, 4:1:5 (measure pH value)
c) 40 mg/ml WX-UK1 in 1,2-propanediol/ethanol, anhydrous
d) 40 mg/ml WX-UK1 in PG/ethanol/40 mM sodium citrate, 4:1:5 (adjust pH value to that of solution (b))
e) 40 mg/ml WX-UK1 in PG/ethanol/40 mM sodium-acetate buffer, 4:1:5 (adjust pH value to that of solution (b))

In order to produce 80 mM sodium citrate buffer (pH value as above), 1.68 g of citric acid monohydrate were dissolved in 8 ml of 1 N sodium hydroxide and made up with water to 100 ml. The pH value was adjusted with 80 nM sodium hydroxide. 1 mM buffer was obtained by 1/80 dilution and subsequent pH adjustment.

Figure 4:
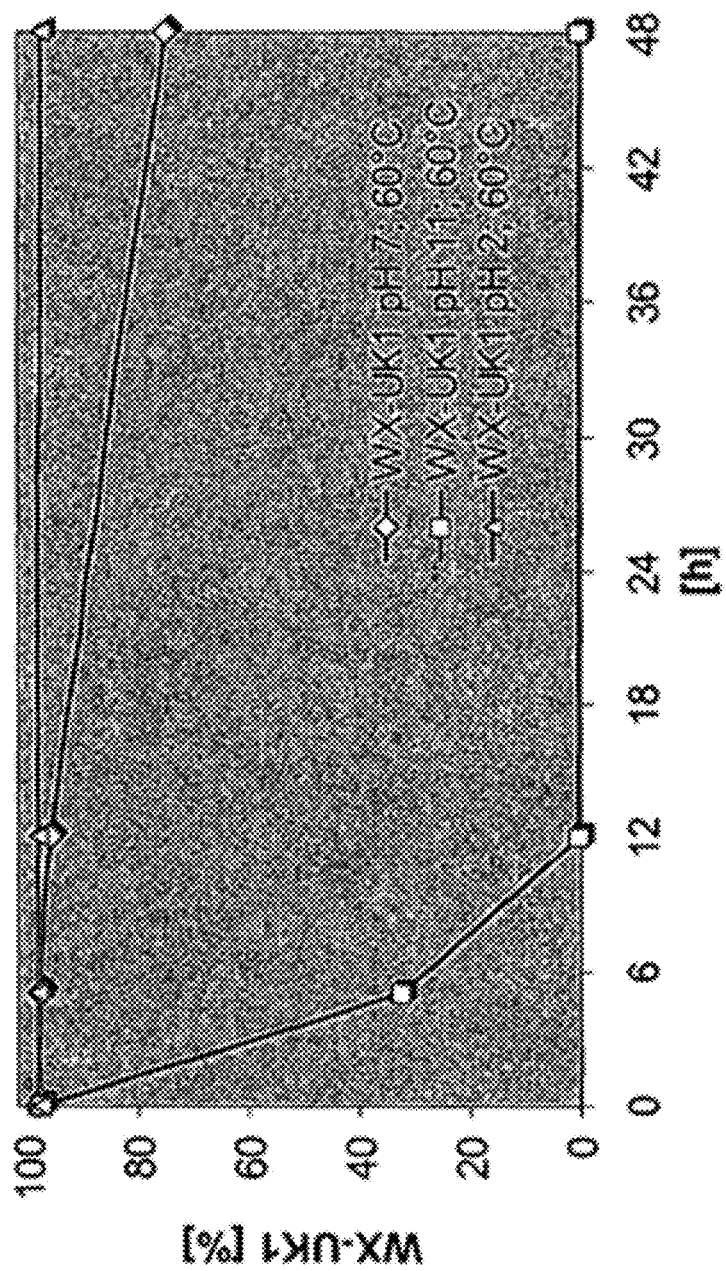
FIG. 4 shows the pH-dependency of WX-UK1 breakdown at 60° C. observed over 48 h.

Sodium acetate and sodium citrate at pH 5 were selected as a parenterally acceptable system for buffering the WX-UK1 formulation and chemical and physical stability were tested relative to the unbuffered formulation and an anhydrous formulation. A phosphate buffer was not used because it was known from earlier investigations that addition of phosphate buffer results in formation of a precipitate in WX-UK1 solutions. The stability study was carried out at 60° C. in order to achieve more rapid breakdown of WX-UK1. The citrate-buffered WX-UK1 solution very rapidly threw a precipitate, which, like the solution supernatant, was tested for the purity of WX-UK1. Due to the inadequate physical stability of the sodium citrate-buffered solution and the inadequate chemical stability of the investigated formulation, the stability study for these formulations was terminated after four days. The sodium acetate-buffered WX-UK1 formulation exhibited the greatest physical and chemical stability. The WX-UK1 peak area percentage, determined by a stability-indicating HPLC method, was evaluated (FIG. 4).

Example 4

Stability of Sodium Acetate-Buffered Solutions

Figure 5:
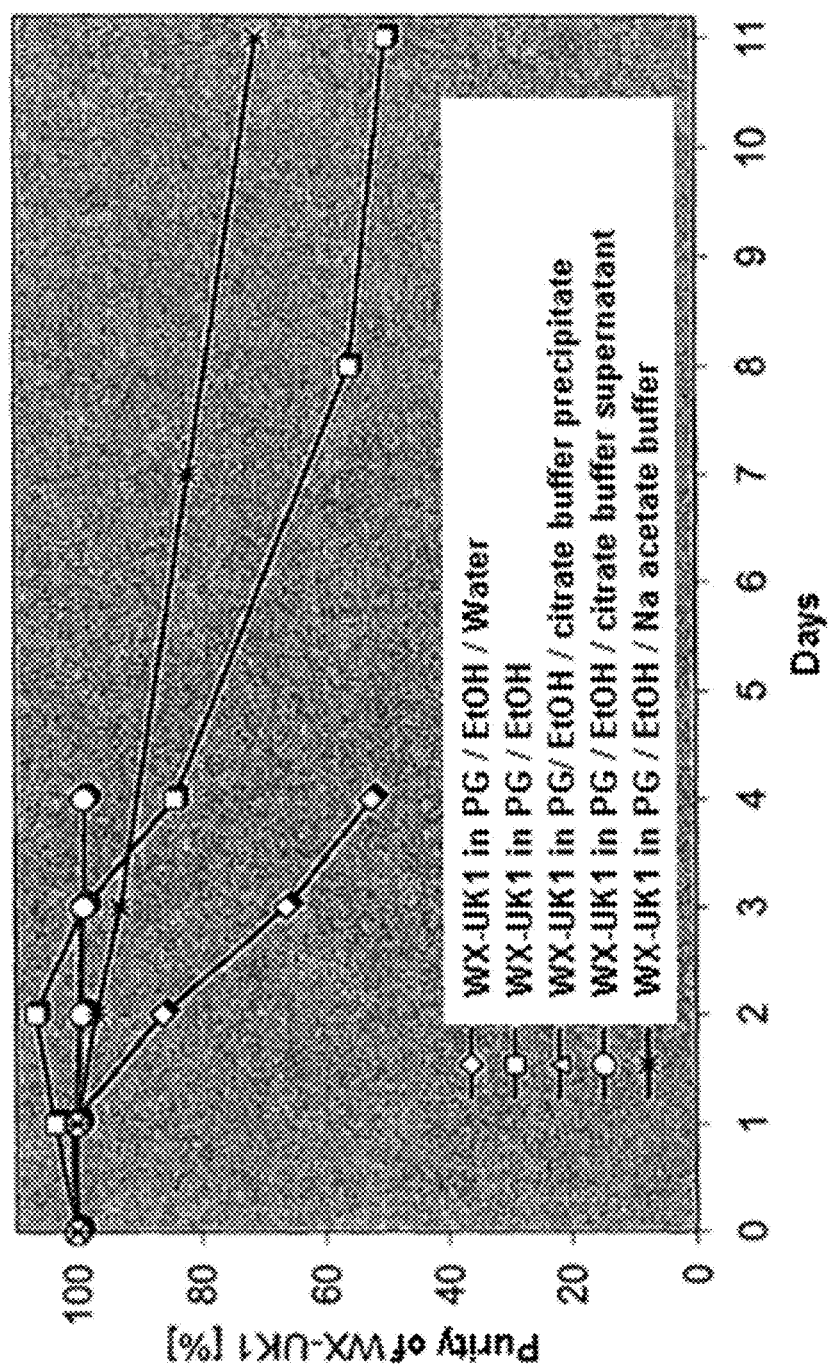
FIG. 5 shows the stability of the individual WX-UK1 formulations at 60° C.

On the basis of these results, sodium acetate in various molarities at pH 5 was selected as a parenterally acceptable system for buffering the WX-UK1 formulation and chemical stability relative to the unbuffered formulation was additionally tested. The stability study was carried out at 60° C. in order to achieve accelerated breakdown of WX-UK1 (FIG. 5). The WX-UK1 peak area percentage, determined by a stability-indicating HPLC method, was evaluated.
Result: A considerable reduction in the rate of breakdown of WX-UK1 can be achieved by buffering the formulation.

Example 5

Stability Study Over Several Months with a Sodium-Acetate-Buffered Formulation

Production of a 200 mM Sodium Acetate Buffer:
821 mg of sodium acetate were dissolved in 50 ml of water and adjusted to pH 5 with concentrated acetic acid and the finished buffer solution was filtered through a Millipore Millex GV 0.22 μm syringe filter.
Production of the 100 mM Sodium Acetate-Buffered WX-UK1 Formulation:
960 mg of WX-UK1 were weighed out into a vessel and 9.6 ml of propylene glycol were added, followed by 2.4 ml of ethanol. This solution was made up with 7 ml of 200 mM sodium acetate buffer and stirred until WX-UK1 passed into solution and the solution exhibited slight opalescence. The remaining sodium acetate buffer (5 ml) was then added. The solutions were divided into 1 ml aliquots and then stored at 40° C.: the purity and WX-UK1 content of the solution were in each case analysed after a period of 2, 4, 6, 8 and 12 weeks. To this end, 250 μl of the WX-UK1 solution were transferred into a 100 ml measuring flask and made up with water/acetonitrile (50:50 vol/vol) to the graduation mark (concentration: approx. 0.1 mg/ml of WX-UK1). 20 μl of this dilution of the WX-UK1 solution were then analysed by means of a stability-indicating HPLC method (see Annex).

The WX-UK1 content was evaluated relative to two WX-UK1 standard solutions using the following formula:

$$WX\text{-}UK1\ [mg/ml] = \frac{Area_{PL} \times (W_{St1} + W_{St2}) \times C_{St}}{(Area_{St1} + Area_{St2}) \times 100 \times V_{PL}}$$

Figure 6:
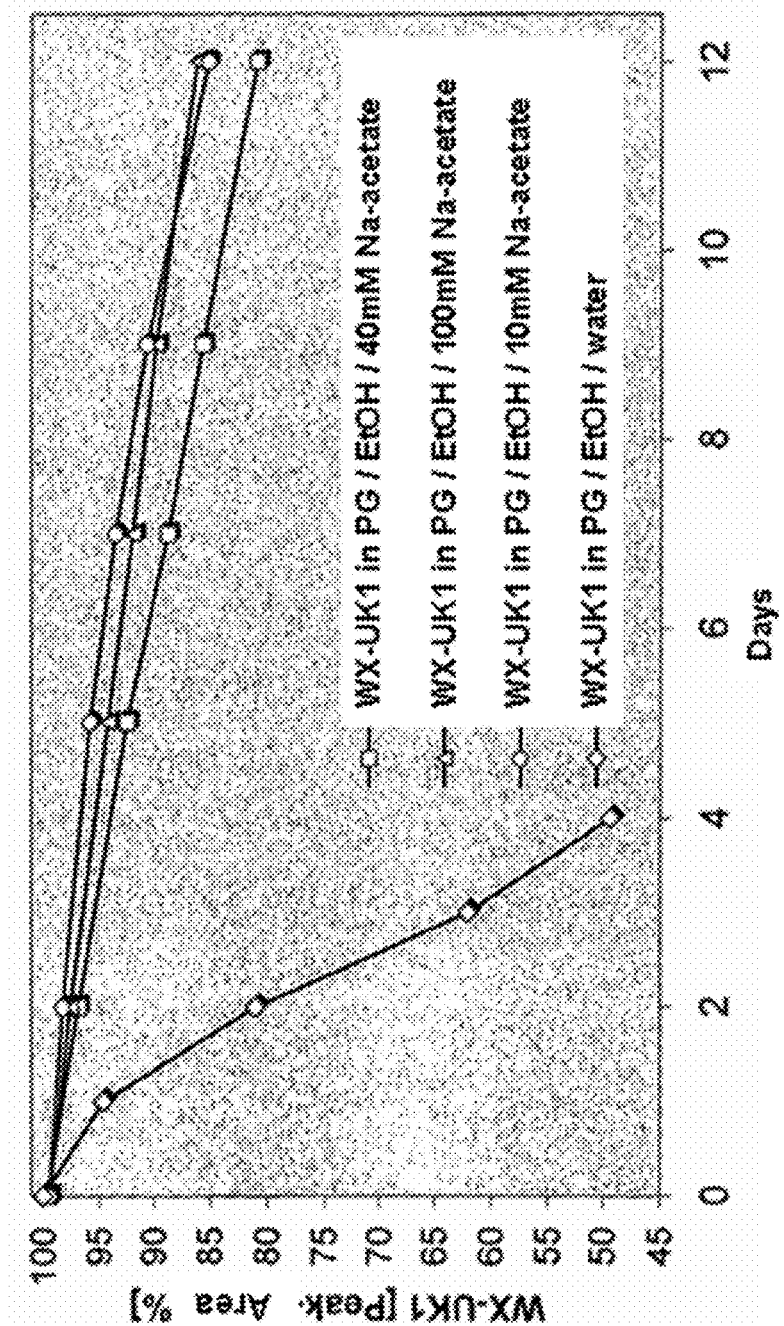
FIG. 6 shows the stability of the buffered WX-UK1 formulations in comparison with the unbuffered solution.
Figures 7A, 7B:
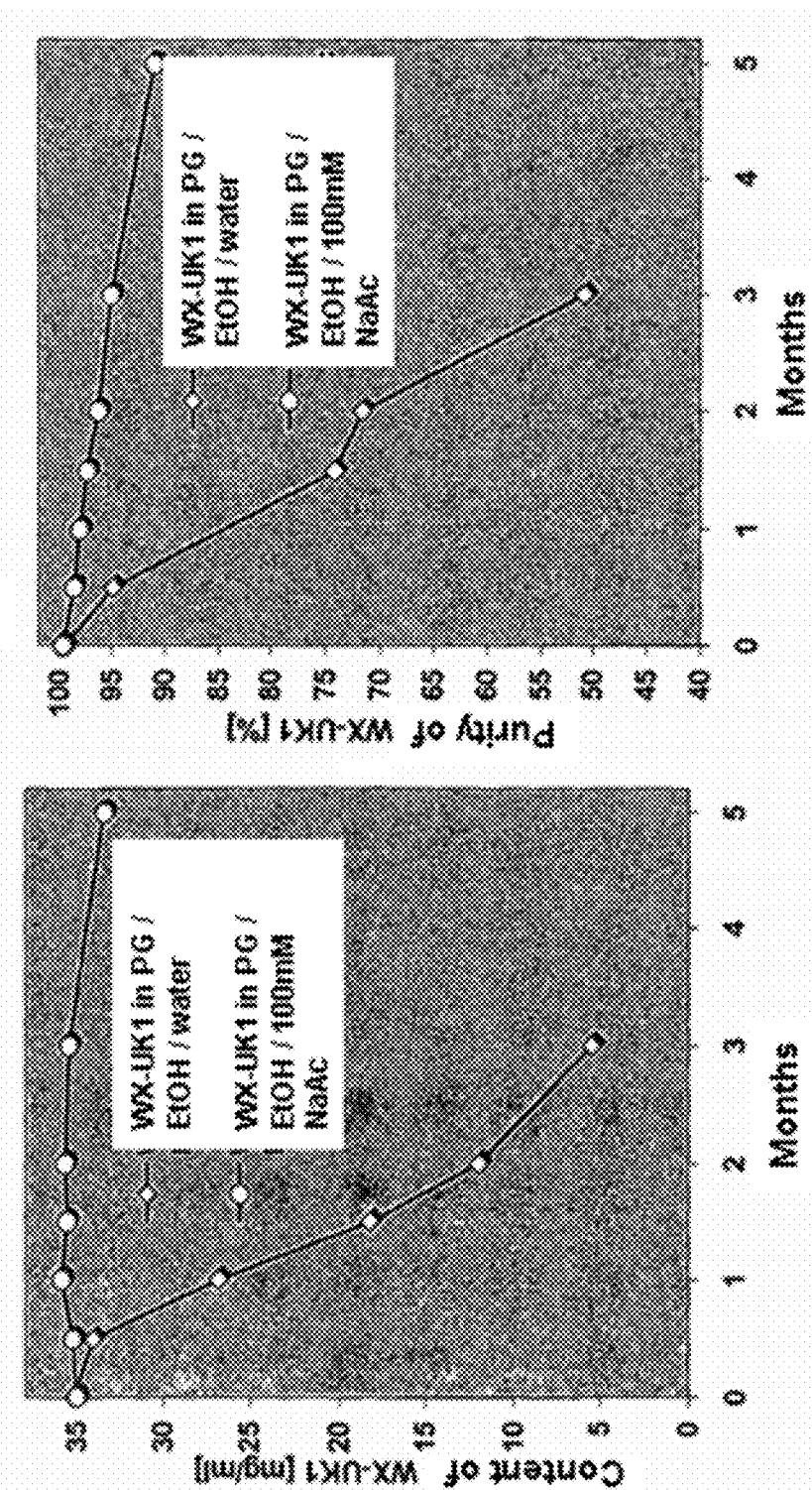
FIGS. 7A and 7B show the purity (FIG. 7B) and content (FIG. 7A) of the WX-UK1 formulations at 40° C. over 5 months.

$Area_{PL}$ = Test solution area (WX-UK1 peak) $[mAU^*s]$
$Area_{St1}$ = Standard I area (WX-UK1 peak) $[mAU^*s]$
$Area_{St2}$ = Standard II area (WX-UK1 peak) $[mAU^*s]$
$W_{St1}$ = Weight of standard I $[mg]$
$W_{St2}$ = Weight of standard II $[mg]$
$C_{St}$ = Content of standard $[\%]$
$V_{PL}$ = Volume of injection solution used $[ml]$ FIG. 6 shows the variation over time in both the purity of the formulations and the content of WX-UK1. It is clear that both the purity and the content of the buffered WX-UK1 formulation remain very stable, in contrast to the unbuffered formulation (FIG. 6).

Example 6

The WX-UK1 Formulation (40 mg/ml) is Produced Using the Following Method

| | |
|---|---|
| WX-UK1 | 40 mg |
| Propylene glycol | 0.4 ml |
| Absolute ethanol | 0.1 ml |
| Water | make up to 1 ml |

WX-UK1 was weighed out into a vessel and propylene glycol was added, followed by ethanol. This solution was made up with 0.3 ml of water and stirred until WX-UK1 passed into solution or the solution exhibited slight opalescence. The remaining water was then added.

Example 7

The Sodium Acetate-Buffered WX-UK1 Formulation (40 mg/ml) was Produced Using the Following Method

| | |
|---|---|
| WX-UK1 | 40 mg |
| Propylene glycol | 0.4 ml |
| Absolute ethanol | 0.1 ml |
| Sodium acetate buffer (200 mM) | make up to 1 ml |

WX-UK1 was weighed out into a vessel and propylene glycol was added, followed by ethanol. This solution was made up with 0.3 ml of 200 mM sodium acetate and stirred until WX-UK1 passed completely into solution or the solution exhibited slight opalescence. The remaining acetate buffer was then added.

Example 8

Stability-Indicating HPLC Method for Verifying the Stability of the WX-UK1 Formulations

| Apparatus and conditions: | |
|---|---|
| HPLC system: | Agilent 1100 |
| Column type: | LUNA C8(2) 5 μm, 250 mm, 4.6 mm ID |
| | or |
| | Kromasil 100 C18 5 μm, 250 mm, 4 mm ID |
| Detection wavelength: | UV 205 nm |
| Sample injector temperature: | 4° C. |
| Column temperature: | 40° C. |
| Injection volume: | 20 μl |
| Type of system: | Gradient system |
| Flow rate: | 1 ml/min |
| Run time: | 44 min |
| Mobile solvents: | A: buffer pH = 5.00 ± 0.05 (25 mM Na phosphate) |
| | B: acetonitrile |

-continued

| Gradient: | | | |
|---|---|---|---|
| Time [min] | A [%] | B [%] | |
| 0 | 75 | 25 | |
| 30 | 28 | 72 | |
| 31 | 10 | 90 | |
| 36 | 10 | 90 | |
| 37 | 75 | 25 | |
| 44 | 75 | 25 | end |

| | |
|---|---|
| Materials to be used: | Water for chromatography (gradient grade)<br>Acetonitrile for chromatography<br>Orthophosphoric acid, 85% Suprapur<br>Disodium hydrogenphosphate analytical grade (>99.99%)<br>25 mM sodium phosphate buffer pH = 5.00 ± 0.05<br>(3.55 g $Na_2HPO_4$ were made up with water to 1000 ml. The pH value was adjusted to pH = 5.00 ± 0.05 with $H_3PO_4$) |
| Sample preparation: | |
| WX-UK1 test solution: | 25 μl of WX-UK1 (40 mg/ml) concentrate were diluted with 975 μl of water/acetonitrile (50:50 vol/vol). 100 μl of this dilution solution were diluted with 900 μl of water/acetonitrile (50:50 vol/vol) (c is approx. 0.1 mg/ml WX-UK1). |

Example 9

HPLC-MS Method for Identifying the Decomposition Products of UK1 Formulations

| Apparatus and conditions: | |
|---|---|
| HPLC system: | Waters Alliance: 2695 separation module; 2487 UV-VIS detector |
| MS detector: | Micromass ZQ: single quadrupole MS detector |
| Column type: | Symmetry C18 3.5 μm; 2.1 × 100 mm |
| Detection wavelength: | UV 215 nm |
| Sample injector temperature: | 4° C. |
| Column temperature: | 35° C. |
| Injection volume: | 20 μl |
| Type of system: | Gradient system |
| Flow rate: | 0.5 ml/min |
| Run time: | 16 min |
| Mobile solvents: | A: $NH_4Ac$ buffer/ACN 72/25 (vol/vol)<br>B: $NH_4Ac$ buffer/ACN 30/70 (vol/vol)<br>C: Methanol |

| Gradient: | | | | |
|---|---|---|---|---|
| Time [min] | A [%] | B [%] | C [%] | |
| 0 | 100 | 0 | 0 | |
| 10 | 0 | 100 | 0 | |
| 11 | 0 | 20 | 80 | |
| 12 | 0 | 20 | 20 | |
| 13 | 100 | 0 | 0 | |
| 16 | 100 | 0 | 0 | end |

| | |
|---|---|
| Materials to be used: | Water for chromatography (gradient grade)<br>Acetonitrile for chromatography (gradient grade)<br>Methanol (HPLC gradient grade)<br>Glacial acetic acid (Suprapur)<br>Ammonium acetate (HPLC grade)<br>50 mM $NH_4Ac$: Make up 3.85 g of $NH_4Ac$ to 1000 ml with water. pH adjustment to 5 with glacial acetic acid |

The invention claimed is:

1. A stable pharmaceutical formulation for inhibiting urokinase comprising;
   as an active ingredient Nα-(2,4,6-triisopropylphenylsulfonyl)-3-amidino-(L)-phenylalanine-4-ethoxycarbonylpiperazide, wherein the active ingredient is present in a concentration of 40 mg/ml,
   a sodium acetate buffer present in a concentration of 40 mM,
   and a mixture of propylene glycol:ethanol:40 mM sodium acetate buffer in a mixing ratio of 4:1:5 in an amount of approximately 45-55% relative to the entire formulation,
   wherein the formulation exhibits at room temperature a pH value of 5.

* * * * *